(12) United States Patent
Kihara

(10) Patent No.: US 10,511,501 B2
(45) Date of Patent: Dec. 17, 2019

(54) ANALYZING DEVICE SYSTEM AND PROGRAM FOR THE SYSTEM

(71) Applicant: SHIMADZU CORPORATION, Kyoto-shi, Kyoto (JP)

(72) Inventor: Takayuki Kihara, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 198 days.

(21) Appl. No.: 15/523,826

(22) PCT Filed: Nov. 6, 2014

(86) PCT No.: PCT/JP2014/079439
§ 371 (c)(1),
(2) Date: May 2, 2017

(87) PCT Pub. No.: WO2016/071987
PCT Pub. Date: May 12, 2016

(65) Prior Publication Data
US 2017/0317900 A1 Nov. 2, 2017

(51) Int. Cl.
*H04L 12/26* (2006.01)
*G01N 35/00* (2006.01)
*G06F 9/46* (2006.01)

(52) U.S. Cl.
CPC ..... *H04L 43/065* (2013.01); *G01N 35/00871* (2013.01); *G06F 9/46* (2013.01);
(Continued)

(58) Field of Classification Search
CPC .............. H04L 43/065; H04L 43/045; G01N 35/00871; G01N 2035/00881;
(Continued)

(56) References Cited

U.S. PATENT DOCUMENTS 7,908,313 B2 * 3/2011 Lurie .................... G06F 9/5072
709/202
9,581,573 B2 * 2/2017 Aota ...................... G01N 30/34
(Continued)

OTHER PUBLICATIONS

Shimadzu Corp., "i-Series liquid chromatography—Frees operators from the laboratory ICM (Interactive Communication Mode)", [online], [retrieved Oct. 29, 2014], internet.
(Continued)

*Primary Examiner* — Todd L Barker
(74) *Attorney, Agent, or Firm* — Sughrue Mion, PLLC

(57) ABSTRACT

An operator creates a function table on an analyzing device, a computer for analysis or a server. In the function table, an instruction is described which includes designation of the computer(s) for analysis or the server, and a process to be executed by the designated computer(s) for analysis or server, and optionally includes parameter information required for execution. For analysis, the function table is displayed on a display screen of the analyzing device. When the operator selects an instruction in the table and instructs execution, the analyzing device causes the designated computer(s) for analysis or server described in the instruction to execute a process associated with the instruction. Such instruction can include a process of powering on the computer(s) for analysis. By previously describing expected processes and the computer(s) for analysis scheduled to perform the processes the processes to be executed can be instructed from the analyzing device.

11 Claims, 5 Drawing Sheets

(52) U.S. Cl.
CPC .... *H04L 43/045* (2013.01); *G01N 2035/0091* (2013.01); *G01N 2035/00881* (2013.01)

(58) Field of Classification Search
CPC . G01N 2035/0091; G01N 2035/00871; G01N 33/48792; G01N 33/4972; G01N 33/54386; G01N 33/94; G06F 9/46; G06F 13/16; G06F 13/4068; G06F 13/4265; G16B 30/00; H01L 21/768; H01L 21/68886
See application file for complete search history.

(56) References Cited

U.S. PATENT DOCUMENTS

| | | | | |
|---|---|---|---|---|
| 9,679,104 | B2* | 6/2017 | van Rooyen | H01L 21/76886 |
| 2002/0080174 | A1* | 6/2002 | Kodosky | G06F 8/34 |
| | | | | 715/762 |
| 2002/0083082 | A1* | 6/2002 | Fujieda | G06F 17/50 |
| 2011/0055385 | A1* | 3/2011 | Tung | G06F 9/5072 |
| | | | | 709/224 |
| 2013/0145299 | A1* | 6/2013 | Steimle | G16H 10/40 |
| | | | | 715/771 |
| 2014/0039826 | A1* | 2/2014 | Valdes | G01R 31/2822 |
| | | | | 702/123 |
| 2014/0173625 | A1* | 6/2014 | Kumar | G06F 9/4843 |
| | | | | 718/106 |
| 2014/0207874 | A1* | 7/2014 | Soorianarayanan | H04L 65/403 |
| | | | | 709/206 |
| 2016/0077091 | A1* | 3/2016 | Tyrrell | G01N 33/48792 |
| | | | | 436/501 |

OTHER PUBLICATIONS

Written Opinion dated Feb. 10, 2015 in application No. PCT/JP2014/079439.

* cited by examiner

| ID | Function name | Target PC identifier | Entity of function (name of program to be executed and argument) | The number of parameters |
|---|---|---|---|---|
| 1 | Power on PC | 192.168.1.1 | C:¥Program Files¥WakeUpPC.exe "192.168.100.1" | 0 |
| 2 | Log on to PC | 192.168.1.1 | C:¥Program Files¥LogonPC.exe "192.168.100.1" | 2 |
| 3 | Activate analysis program | 192.168.100.1 | C:¥Program Files¥OpenAnalysis.exe (No argument) | 2 |
| 4 | Download routine method into analyzing device | 192.168.100.1 | C:¥Program Files¥SetMethod001.exe (No argument) | 0 |
| 5 | Log off of PC | 192.168.100.1 | C:¥Program Files¥LogoffPC.exe (No argument) | 0 |

| Type of parameter 1 | Description of parameter 1 | Type of parameter 2 | Description of parameter 2 | ... | ... |
|---|---|---|---|---|---|
| – | – | – | – | – | – |
| 1 | Enter OS logon user ID. | 2 | Enter OS logon password. | – | – |
| 1 | Enter user ID of analysis program. | 2 | Enter logon password of analysis program. | – | – |
| – | – | – | – | – | – |
| – | – | – | – | – | – |

PARAMETER TYPE
 1  CHARACTER STRING
 2  PASSWORD CHARACTER STRING.   ENTERED CHARACTER IS DISPLAYED AS *

ANALYZING DEVICE SYSTEM AND PROGRAM FOR THE SYSTEM

CROSS REFERENCE TO RELATED APPLICATIONS

This application is a National Stage of International Application No. PCT/JP2014/079439, filed Nov. 6, 2014, the contents of which are incorporated herein by reference in its entirety.

TECHNICAL FIELD

The present invention relates to a system including an analyzing device connected to a computer via a network and used together with the computer, and to a program used in the system.

BACKGROUND ART

In modern analysis, analysis conditions and data obtained by the analysis are becoming more complicated. Thus, it is often the case that a general computer on which various tools are available and which has a high data processing capability is connected to an analyzing device. In that case, analysis conditions are set through the computer, the analyzing device is controlled through the computer, data obtained by the analyzing device is transferred to the computer, and the data is analyzed by the computer. When a computer is connected to an analyzing device, it is common practice to design the system to make various operations easier on the computer side (e.g., Patent Literature 1).

However, in a case where a single computer is used to control plural analyzing devices and collectively analyze data items obtained by the analyzing devices on the single computer, or a case where the analyzing device or the computer requires a special environment (temperature, humidity, cleanliness, etc.), the analyzing device and the computer are installed at separate sites or in different rooms. In such a case, an operator first has to make operations on the analyzing device such as placing a sample on the analyzing device and making the hardware setting on the analyzing device, and then the operator has to move to the site (room) where the computer is installed to operate the computer.

One approach to address this is to make a specific simple operation on an input unit (operation panel) of the analyzing device to execute a predetermined function of the computer (Non Patent Literature 1). According to this approach, by pressing (touching) an analysis start button on the operation panel of the analyzing device, the computer executes a predetermined batch process for an analysis.

CITATION LIST

Patent Literature

[Non Patent Literature 1] Shimadzu Corp., "i-Series liquid chromatography—Frees operators from the laboratory ICM (Interactive Communication Mode)", [online], [retrieved Oct. 29, 2014], internet

SUMMARY OF INVENTION

Technical Problem

The above-described conventional art allows the operator to send an analysis instruction to the computer located at a separate site without leaving from the analyzing device, which increases the operator's convenience. However, it is presumed that the computer is active at that time and the analysis program is in operation on the computer. If such presumption is not true, the operator still needs to move to the personal computer and operate it at the site.

In a case where various plural analyses are required to be performed while changing the analysis sample and the conditions of the analyzing device, the operator needs to alternately repeat a preparatory operation on the analyzing device and an analysis command operation on the computer. Accordingly, the analyst must move between the analyzing device and the computer very frequently.

An object to be achieved by the present invention is to provide a system that improves the convenience of operations of a computer for analysis at an analyzing device in a case where the computer that performs analysis processing by using the analyzing device is provided separately from the analyzing device.

Solution to Problem

An analyzing device system according to the present invention made in order to achieve the object includes:
  a) a network;
  b) an analyzing device and one or a plurality of computers for analysis, and/or a server that are connected to the network;
  c) function table creating means provided in any of the analyzing device and one or the plurality of computers for analysis, and/or the server, and for creating a function table describing an instruction that includes designation of any of one or the plurality of computers for analysis and/or the server, and a predetermined process to be executed by the designated computer(s) for analysis or the server, and optionally includes parameter information required for execution; and
  d) function table executing means provided in the analyzing device, and for storing the function table, displaying the function table on a display screen, and executing the instruction according to an operation by an operator.

In the analyzing device system according to the present invention, the server is a computer having a function capable of controlling the computer for analysis connected to the network, including powering on the computer for analysis. Consequently, in an environment where the analyzing device system according to the present invention is used, the server is always powered on. Two or more servers may be provided. In the case where there are a plurality of computers for analysis, one or the plurality of computers may be used as a server.

In an analyzing device system according to the present invention, an operator or other person to analyze a sample creates a function table on an analyzing device, on a computer for analysis or on a server by using function table creating means provided in the analyzing device, computer for analysis or server. In the function table, the operator or other person describes an instruction that includes designation of the computer for analysis or the server, and a process to be executed by the designated computer for analysis or server, and optionally includes parameter information required for execution. The function table may include one or more instructions. The function table thus created is stored in the function table executing means provided in the analyzing device. When the function table is created by using the function table creating means on the computer for analysis or the server, the function table is transferred to the analyzing device via the network and stored in the function table executing means.

The function table executing means displays the function table thus stored on the display screen of the analyzing device. When an operator selects an instruction in the displayed function table and commands execution of the instruction, the analyzing device makes the designated computer for analysis or server described in the instruction execute a process associated with the instruction.

In the analyzing device system according to the present invention, the instruction can include a process of powering on a certain computer for analysis. In this case, the server is to be designated and executes such a process.

The present invention can be configured as the analyzing device system as described above. Alternatively, the present invention can also be configured as a program executed in the analyzing device system that includes such an analyzing device and one or a plurality of computers for analysis, and/or a server. In this case, the program according to present invention includes:

a) a function table creator provided in any of the analyzing device and one or the plurality of computers for analysis, and/or the server, and for creating a function table describing an instruction that includes designation of any of one or the plurality of computers for analysis and/or the server, and a predetermined process to be executed by the designated computer(s) for analysis or the server, and optionally includes parameter information required for execution; and b) a function table executor provided in the analyzing device, and for storing the function table, displaying the function table on a display screen, and executing the instruction according to an operation by an operator.

Advantageous Effects of Invention

In the analyzing device system according to the present invention, the operator can send various instructions to the computer for analysis located at another site without leaving from the analyzing device. Furthermore, such instructions may include a process of powering on the computer for analysis. By previously describing expected processes and the computers for analysis scheduled to perform the processes in the function table, the processes to be executed can be instructed from the analyzing device. Consequently, the operator can achieve most of the operations including complicated analysis operations near the analyzing device, and the convenience of the analyzing device is significantly improved.

BRIEF DESCRIPTION OF DRAWINGS

FIG. 4A is a display screen containing a button for displaying a function table, and FIG. 4B is a display screen of the function table.

FIG. 5A is a logon user ID input screen, and FIG. 5B is a logon password input screen.

FIG. 6 is a diagram illustrating an example of a structure and content of the function table.

FIG. 7A is a screen for displaying a progress status of a process, and FIG. 7B is a screen for displaying a result of the process (failure).

DESCRIPTION OF EMBODIMENTS

Figure 1:
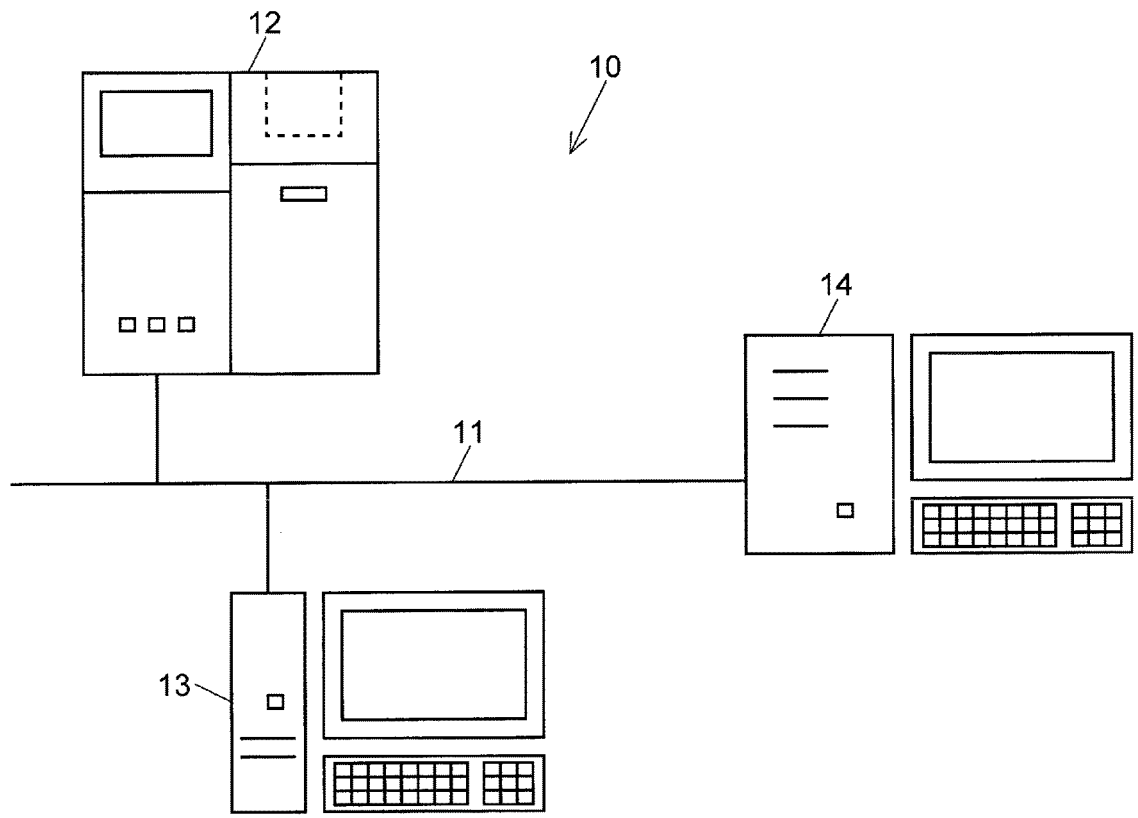
FIG. 1 is an overall schematic configuration diagram of a chromatograph analyzing device system according to one embodiment of the present invention.

Hereinafter, a chromatograph analyzing device system as an embodiment of an analyzing device system according to the present invention will be described with reference to the drawings. As shown in FIG. 1, the chromatograph analyzing device system 10 of this embodiment includes a chromatograph analyzing device 12, a personal computer for analysis 13, and a server 14, which are connected to each other via a network 11. The server 14 is always powered on. A configuration may be employed in which the personal computer for analysis 13 may also function as the server 14 without separately providing the server 14. Another analyzing device, personal computer for analysis, server, and the like other than the above configuration components may be connected to the network 11 of the chromatograph analyzing device system 10 of the embodiment.

Figure 2:
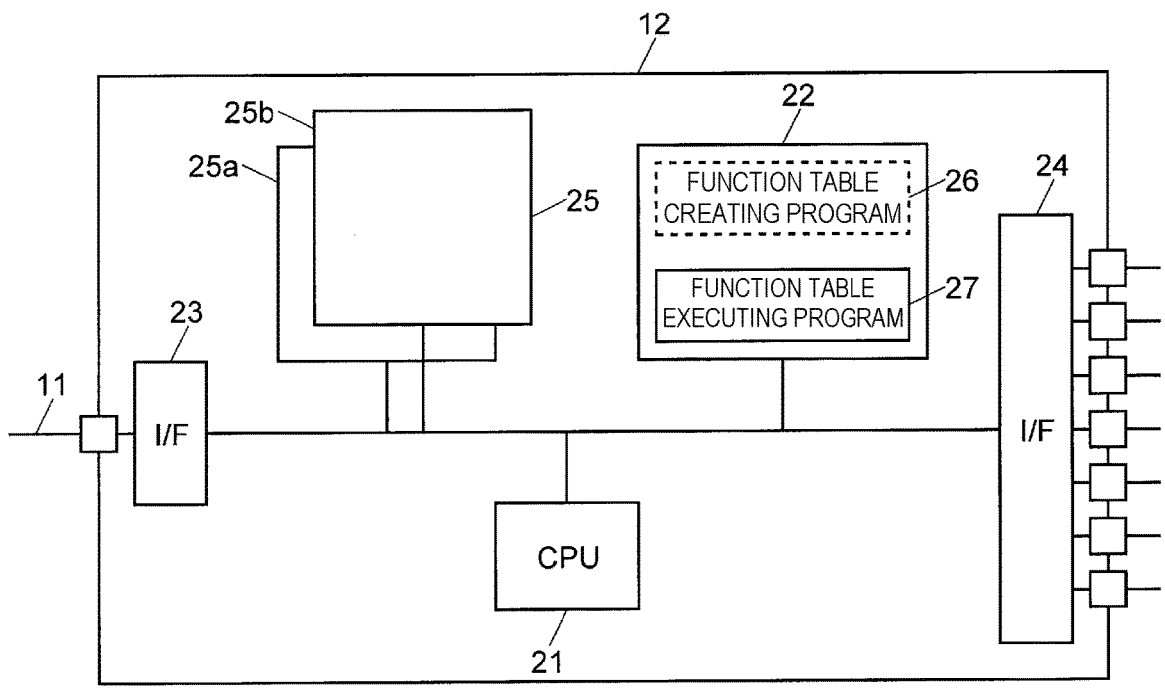
FIG. 2 is a schematic configuration diagram of an analyzing device included in the chromatograph analyzing device system of the embodiment.

As shown in FIG. 2, the chromatograph analyzing device 12 includes, in addition to a central processing unit (CPU) 21 and a storage unit 22, an interface (I/F) 23 with the network 11, an interface (I/F) 24 with various device units such as a column oven, a pump, and a sample injector, and an operation panel 25 including a display unit 25a and an input unit 25b. The storage unit 22 stores a function table creating program 26 and a function table executing program 27, which are described later.

Figure 3:
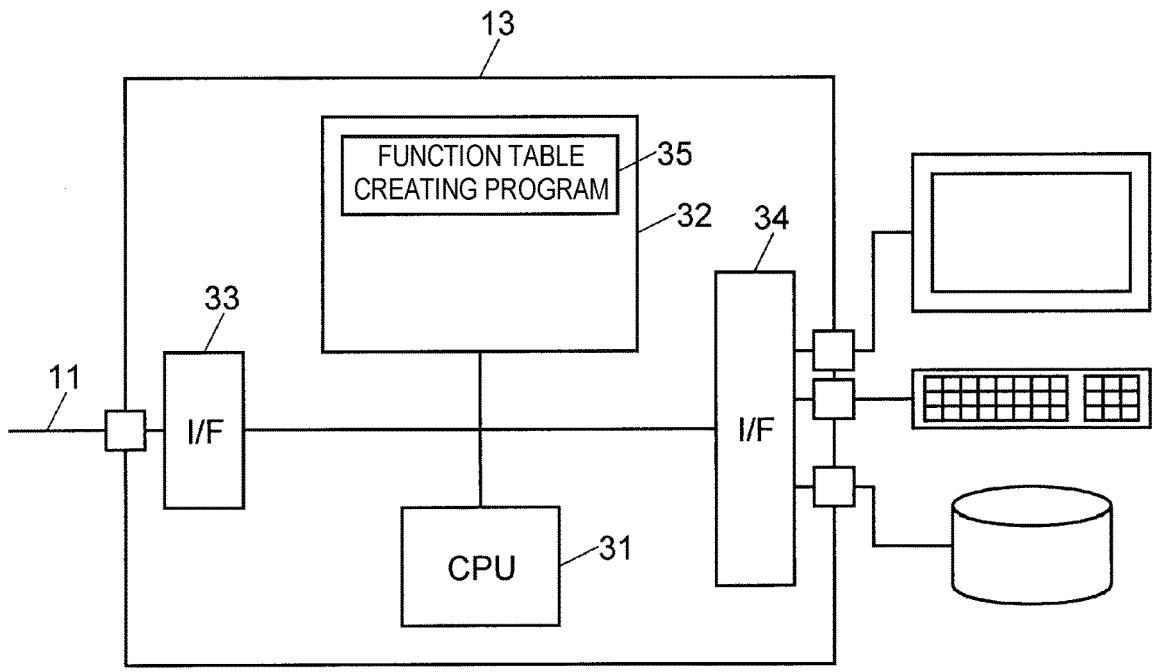
FIG. 3 is a schematic configuration diagram of a computer for analysis included in the chromatograph analyzing device system of the embodiment.

As shown in FIG. 3, the personal computer for analysis 13 includes, in addition to a central processing unit (CPU) 31 and a storage unit 32, an interface (I/F) 33 with the network 11 and an interface (I/F) 34 with a display, an input device and an external storage device and the like. The storage unit 32 stores a function table creating program 35 described later. The configuration of the server 14 is substantially the same as this configuration.

In the chromatograph analyzing device system 10 having such a configuration, procedures in which an operator on the analyzing device 12 side makes the personal computer for analysis 13 execute various analyses will be described. Hereinafter, the description will be made on a case where the server 14 is provided separately from the personal computer for analysis 13.

First, the operator activates the function table creating program 35 at the personal computer for analysis 13 and creates a function table. The function table creating program 35 executed by the CPU 31 corresponds to function table creating means of the present invention. The function table creating program is installed also in the server 14. The operator may create the function table on the server 14. The function table creating program 26 for the analyzing device is installed also in the analyzing device 12. However, input is required through the operation panel 25. Consequently, the program may not be suitable to create a complicated function table. It may be practical to correct a function table having already been created.

An example of the function table is shown in FIG. 6. This function table is horizontally long (each row is long) and so the function table is shown in a vertically divided manner. In the function table 50 of FIG. 6, five instructions are described. Each instruction includes a numeral (ID) for identifying the instruction, the name of the instruction (function name), a computer that is the target of the instruction (the personal computer for analysis 13 or the server 14), a command that is the entity of the function to be executed by the computer, and descriptions pertaining to parameters used for the command. The number of parameters is zero, one, two or more depending on the command. Meanwhile, the length of the function table 50 (length of one row) is set so as to conform with the instruction having the maximum number of parameters among the instructions that can be described in the function table 50.

The instruction (ID=1) on the first row of the function table 50 of FIG. 6 has a function of powering on the personal computer for analysis 13. Thus, the target computer is the server 14, and the IP address (192.168.1.1) of the server is described as data for identifying this server. A command to the server 14 is "Power on personal computer for analysis". The instruction [C:\Program Files\WakeUpPC.exe "192.168.100.1"] including the IP address for identifying the personal computer for analysis 13 as an argument of this command is described. The entity of the program executed according to such a command (in this example, "WakeUpPC.exe") can be created by a user or a program developer. Alternatively, a program can be newly created by the manufacturer of the analyzing device according to the usage of the user, or an existing program on the market can be used.

The instruction (ID=2) on the second row has a function "remotely logging on to the personal computer for analysis 13 through the server". The target computer is also the server 14. The IP address and a command [C:\Program Files\LogonPC.exe "192.168.100.1"] that means "remotely logging on to personal computer for analysis" are described. To this command, two parameters for displaying screens for entering the user ID and password for logon are added. For the first parameter (enter user ID) of these parameters, a type symbol 1 meaning "display character string" is given, and for the second parameter (enter password), a type symbol 2 meaning "display entered character as '*' (asterisk)" is given.

Figure 5A:
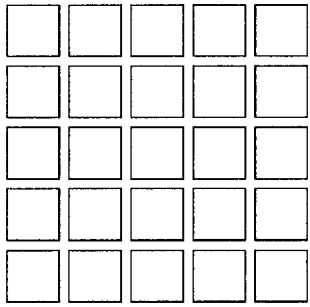
FIG. 5A and FIG. 5B are examples of parameter input screens displayed on the operation panel of the analyzing device.
Figure 5B:
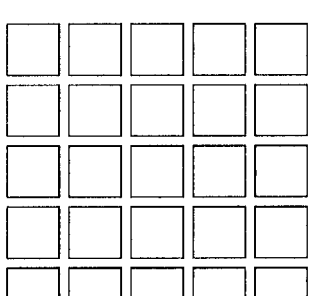

The instruction (ID=3) on the third row is an instruction for activating the analysis program on the personal computer for analysis 13. Thus, the target of the instruction is the personal computer for analysis 13. As with the instructions on the second row, there are two parameters for user ID and password input screens. FIG. 5A shows an example of the user ID input screen for logging on to the analysis program. FIG. 5B shows an example of the password input screen. On each of these screens, a software keyboard for entering characters (numerals) is displayed on a right-hand side.

The instruction (ID=4) on the fourth row is an instruction "download a routine analysis method into this analyzing device 12", and the target is the personal computer for analysis 13. According to a command [C:\Program Files\SetMethod001.exe], the routine analysis method is downloaded into the device from the personal computer for analysis 13. This command does not have any argument or parameter.

The instruction (ID=5) on the fifth row is an instruction for logging off the personal computer for analysis 13. This instruction does not have any argument or parameter.

The function table 50 thus created is transferred from the personal computer for analysis 13 to the analyzing device 12, and is stored in the storage unit 22. The table is also transferred to the server 14, and is stored in the storage unit. The analyzing device 12 queries the personal computer for analysis 13 or the server 14, upon activation or at appropriate timing, about the version of the function table, and downloads the latest one from the query target when the function table held by the device itself is not the latest. Alternatively, the analysing device 12 may download the function table in the server 14 upon each activation or at each appropriate timing without comparing versions.

Figure 4A:
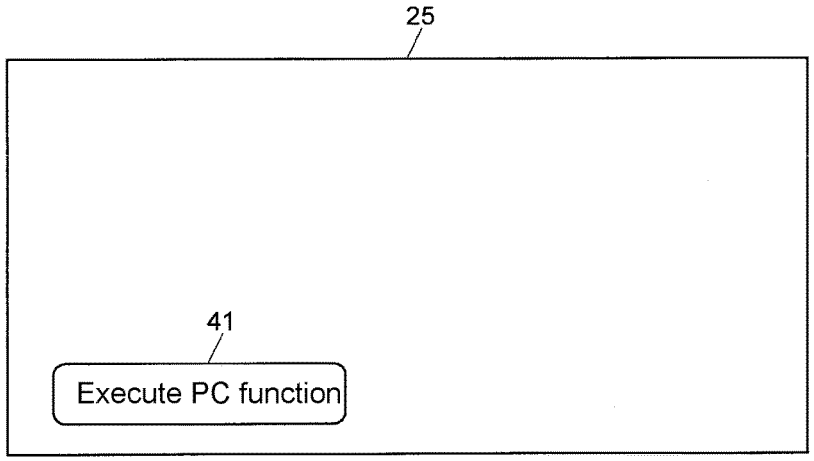
FIG. 4A and FIG. 4B are display screens displayed on an operation panel of the analyzing device.
Figure 4B:
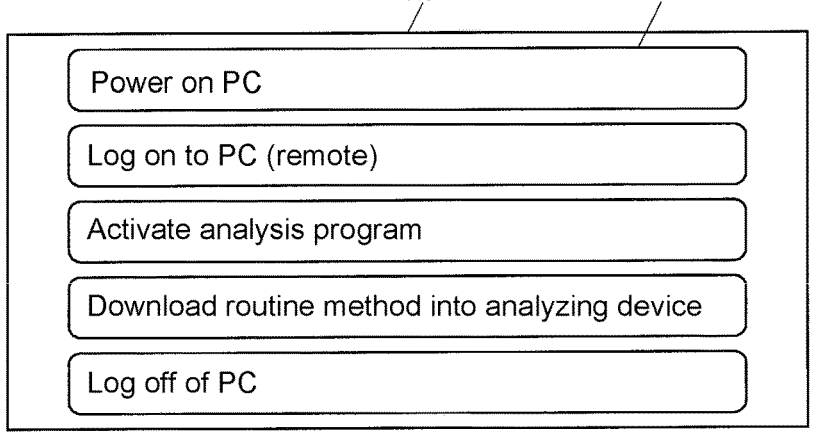

When performing analysis at the analyzing device 12, the operator operates a predetermined button on the operation panel 25 for displaying a menu for executing the functions of the server 14 or the personal computer for analysis 13 (PC). More specifically, as shown in FIG. 4A, a button (function menu displaying button) 41 that is "Execute PC function" among various displays (for the sake of convenience of description, the illustration is omitted) on the operation panel 25 of the analyzing device is pressed (touched), thereby activating the function table executing program 27 to display the function menu 42 as shown in FIG. 4B. Each button on the function menu 42 corresponds to each row of the function table 50 of FIG. 6. The operator presses (touches) any button on the function menu 42, thereby the row (instruction) of the function table 50 associated with the corresponding button is executed.

First, when the operator presses the button "Power on PC" on the first row of the function menu 42, the command [C:\Program Files\WakeUpPC.exe "192.168.100.1"] on the first row of the function table 50 is executed by the server 14 which is the target PC. Thus, the personal computer for analysis 13 is powered on through LAN communication. In a case where the personal computer for analysis 13 corresponding to the analyzing device 12 is predetermined, the argument "192.168.100.1" of the command can be generated by the analyzing device 12 itself (called from its storage unit) and added.

Next, when the button "Log on to PC" on the second row is pressed, the screen for prompting the operator to enter the user ID is displayed according to the description in the parameter field of the function table 50. When the operator enters the ID, then a screen for prompting the operator to enter the password is displayed. When the password is entered, the command [C:\Program Files\LogonPC.exe "192.168.100.1"] on the second row of the function table 50 and the character string information on the entered user ID and password are transferred to the 192.168.1.1 (server 14) which is the target PC. As a result, the server 14 executes the command [LogonPC.exe "192.168.100.1"] with the arguments of the user ID and password, and executes an operation of remotely logging on to the PC for analysis 13. The user ID and passwords which are the parameters are used for a logon operation.

In this way, each button of on the function menu 42 in FIG. 4B is sequentially pressed to execute the instruction on each of rows of the function table 50 accordingly. Powering on the personal computer for analysis 13, logging on to the personal computer for analysis 13, activation of the program for analysis, and downloading the analysis method into the analyzing device 12 can be performed at the analyzing device 12. The analysis is performed at the analyzing device 12. After the analysis is executed and finished, the operator may log off of the personal computer for analysis 13 to complete the all analysis operations on the analyzing device 12 side.

Figure 7A:
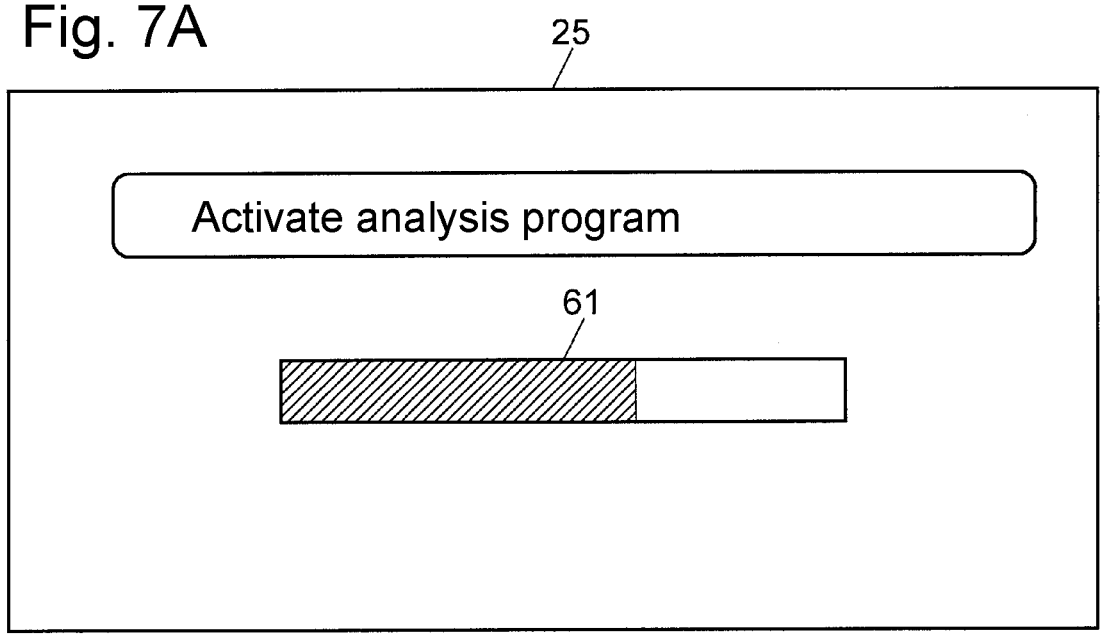
FIG. 7A and FIG. 7B are diagrams of screens displayed on the operation panel of the analyzing device.
Figure 7B:
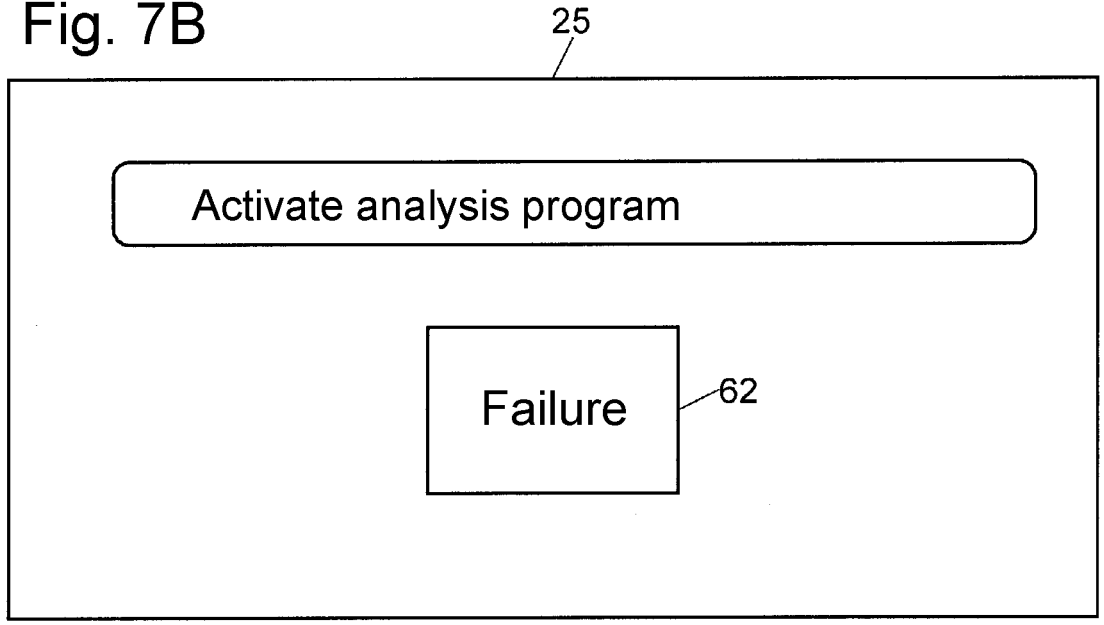

While the various processes are performed at the server 14 and the personal computer for analysis 13 through such button operations on the function menu 42, the progress status and results of the processes (Finished, Failure, etc.) may be displayed on the operation panel 25 of the analyzing device 12. Information on the progress status and results of the processes can be passed from the target computer (the personal computer for analysis 13 or the server 14) to the analyzing device 12 through periodic communication between the target computer and the analyzing device 12. FIG. 7A is an example of a progress bar 61 displayed during execution of "Activate analysis program" on the third row of the function menu 42. This bar allows the progress status of the process to be recognized. FIG. 7B is an example of display 62 in a case of failure in the "Activate analysis program" (e.g., a case of an abnormal end of the analysis program last time and the like). This display allows the operator to take measures of going to the personal computer for analysis 13 in order to find the cause of the failure without uselessly performing the next process "Download routine method into analyzing device".

The embodiment has thus been described mainly on the example where the server 14 is provided separately from the personal computer for analysis 13. In a case where the personal computer for analysis 13 works also as the server 14, the instructions including "Activate PC" and "Log on to PC" cannot be executed but the function table (and the function menu) can be effectively used for the other various instructions including downloading routine method into analyzing device.

REFERENCE SIGNS LIST

10 . . . Chromatograph Analyzing Device System
11 . . . Network
12 . . . Chromatograph Analyzing Device
13 . . . Personal Computer for Analysis
14 . . . Server
21 . . . CPU
22, 32 . . . Storage Unit
25 . . . Operation Panel
25a . . . Display Unit
25b . . . Input Unit
26, 35 . . . Function Table Creating Program
27 . . . Function Table Executing Program
41 . . . Function Menu Displaying Button
42 . . . Function Menu
50 . . . Function Table

The invention claimed is:

1. A chromatograph sample analyzing device system comprising:
  a) a network;
  b) a chromatograph sample analyzing device connected to the network;
  c) one or a plurality of computers and/or a server connected to the network; and
  d) at least one processor configured to:
  create a function table in the one or the plurality of computers and/or the server, the function table including an instruction that designates any of the one or the plurality of computers and/or the server for analysis, and a predetermined process to be executed by at least one of the designated computers and/or the server for analysis,
  store the function table in the chromatograph sample analyzing device and the one or the plurality of computers and/or the server,
  display the function table, provided in the chromatograph sample analyzing device, on a display screen, and
  execute the instruction in the function display on the display,
  wherein, upon activation or at a predetermined time, the chromatograph sample analyzing device is configured to send queries to the one or the plurality of computers and/or the server about a version of the function table and download the latest version from a query target when the function table of the chromatograph sample analyzing device is not the latest version,
  wherein the function table includes an ID information, a function name, a target identifier, an entity of function, and a number of parameters associated with the instruction, and
  wherein the function table including the instruction that makes the computer activate and log onto an analysis program on the computer by using parameter information input by an operator.

2. The chromatograph sample analyzing device system according to claim 1, wherein the computer for analysis serves as the server.

3. The chromatograph sample analyzing device system according to claim 1,
  wherein the at least one processor is further configured to display an execution state or an execution result of the instruction on the display screen of the chromatograph sample analyzing device.

4. The chromatograph sample analyzing device system according to claim 1, wherein the at least one processor is further configured to display a parameter input screen, based on the parameter information required for executing the function table.

5. A non-transitory computer readable medium recording a program to cause at least one processor to:
  a) create a function table in one or a plurality of computers and/or a server, the function table including an instruction that designates any of one or the plurality of computers and/or the server for analysis, and a predetermined process to be executed by at least one of the designated computers and/or the server for analysis,
  b) store the function table in a chromatograph sample analyzing device and in the one or the plurality of computers and/or the server;
  c) display the function table, provided in the chromatograph sample analyzing device, on a display screen; and
  d) execute the instruction in the function display on the display,
  wherein, upon activation or at a predetermined time, the chromatograph sample analyzing device is configured to send queries to the one or the plurality of computers and/or the server about a version of the function table and download the latest version from a query target when the function table of the chromatograph sample analyzing device is not the latest version,
  wherein the function table includes an ID information, a function name, a target identifier, an entity of function, and a number of parameters associated with the instruction, and
  wherein the function table including the instruction that makes the computer activate and log onto an analysis program on the computer by using parameter information input by an operator.

6. The non-transitory computer readable medium according to claim 5, wherein the at least one processor is further configured to display an execution state or an execution result of the instruction on the display screen of the chromatograph sample analyzing device.

7. The non-transitory computer readable medium according to claim 5, wherein the at least one processor is further configured to display a parameter input screen, based on the parameter information required for executing the function table.

8. The chromatograph sample analyzing device system according to claim 1, comprising the computer and the server, wherein the function table includes the instruction that makes the server power on the computer.

9. The chromatograph sample analyzing device system according to claim 1, comprising the computer and the server, wherein the function table including the instruction that makes the server remotely log onto the computer by using parameter information input by an operator.

10. The chromatograph sample analyzing device system according to claim 1, comprising the computer, wherein the function table including the instruction that makes the computer send a method file stored in the computer to the chromatograph sample analyzing device.

11. The chromatograph sample analyzing device system according to claim 1, comprising the computer, wherein the function table including the instruction that makes the computer log off from the computer.

* * * * *